United States Patent [19]

Foery et al.

[11] 4,102,670
[45] Jul. 25, 1978

[54] BETA-HALOGENOETHYL-SILANES AS PLANT GROWTH REGULATORS

[75] Inventors: Werner Foery, Basel; Hans Peter Fischer, Bottmingen, both of Switzerland

[73] Assignee: Ciba-Geigy Corporation, Ardsley, N.Y.

[21] Appl. No.: 727,303

[22] Filed: Sep. 27, 1976

Related U.S. Application Data

[60] Division of Ser. No. 443,180, Feb. 15, 1974, Pat. No. 3,985,780, which is a continuation-in-part of Ser. No. 186,392, Oct. 4, 1971, abandoned.

[30] Foreign Application Priority Data

Oct. 6, 1970 [CH] Switzerland ............... 14797/70
May 14, 1971 [CH] Switzerland ............... 7206/71

[51] Int. Cl.² .................. A01N 9/00; A01N 9/12; A01N 9/20; A01N 9/24
[52] U.S. Cl. .................. 71/98; 71/76; 71/106; 71/105; 71/121; 71/107; 71/123; 71/79; 71/124; 260/448.8 R
[58] Field of Search ............... 260/448.8 R; 71/79, 71/98, 106, 121, 123, 124, 105, 107, 76

[56] References Cited

U.S. PATENT DOCUMENTS 3,928,406 12/1975 Leeper et al. ............... 260/448.8 R Primary Examiner—Paul F. Shaver
Attorney, Agent, or Firm—Harry Falber

[57] ABSTRACT

The present invention relates to new compositions and methods for the regulation of plant growth, especially for fruit abscission, acceleration of ripening and latex discharge and to new active substances of the class of β-halogenoethyl-silanes.

The active substances in the new compositions respond to the formula

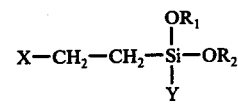

wherein X is chlorine or bromine, Y represents chlorine or the radical —OR₃, each of the radicals R₁, R₂ and R₃ independently represent substituted or unsubstituted alkyl radicals, alkenyl, halogenalkenyl, alkynyl and cycloalkyl radicals, substituted or unsubstituted phenyl and benzyl radicals; one or more of the symbols R₁, R₂ and R₃ can also represent the group —COR₄, wherein R₄ stands for an unsubstituted or substituted alkyl or alkenyl radical, a possible phenyl substituent may itself be substituted or not, for an alkynyl, alkoxyalkyl, alkoxycarbonylalkyl, or phenyl radical optionally substituted or for a heterocyclic radical; R₁ and R₂, also with the signification of —CO—R₄, together with the adjacent atoms, can also form a silicium-containing saturated or unsaturated heterocyclic ring system.

The β-bromoethyl-silanes and the β-chloroethylsilanes of the above formula wherein R₁, R₂, R₃ and R₄ do not represent unsubstituted alkyl radicals with less than 6 carbon atoms, are new compounds.

21 Claims, No Drawings

BETA-HALOGENOETHYL-SILANES AS PLANT GROWTH REGULATORS

This is a division of application Ser. No. 443,180 filed on Feb. 15, 1974 now U.S. Pat. No. 3,985,780 which in turn is a continuation in part of Ser. No. 186,392, filed Oct. 4, 1971 now abandoned.

Compounds which, under certain conditions, release ethylene are known. Such compounds are relatively unstable under the effects of weather, because they are very susceptible to hydrolysis; or they are phytotoxic. β-Halogen-ethyl-phosphonic acid derivatives are described in the South African Patent No. 68/1036 as active substances regulating plant growth. These compounds decompose in and on the plant with the release of ethylene, and are therefore similar in action and range of action to ethylene. By virtue of their very low stability, phosphonic acid derivatives are not able, however, to satisfy the demands made on them. As they are stable only in an acid medium, more precisely in a pH range below 5, the active substance concentrates have to be stabilised by the addition of acids. This acid addition limits, however, the range of application of these active substances with regard to phytotoxic effects. Furthermore, the storage of such sensitive active substance concentrates persents difficulties.

Also known, as herbicidal active substances, are halogenalkyl-methyl-silanes, cp. U.S. Pat. Nos. 3,390,976 and 3,390,977, and J. K. Leasure et al., J. Med. Chem. 9, 949 (1966). β-Chloroethyl-tris-(alkoxy)-silanes and β-chloroethyl-acetoxy-dialkoxy silanes and β-chloroethyl-diacetoxy-alkoxy silanes have been produced by F. W. Boye et al., J. Org. Chem 16, 391 (1951), resp. 17, 1386 (1952).

The U.S. Pat. No. 3,183,076 describes α-chloroethyl-methyldialkoxy-silanes, which can be used for the promotion of germination power, leaf abscission, etc..

In contrast, the β-halogen-ethyl-silanes of this invention affect in a varying manner the growth of parts of plants situated above and below the ground; they are not phytotoxic in the usual concentrations in which they are applied, and have a low toxicity towards warm-blooded animals. The active substances produce no morphological changes or damage which would result in a withering of the plant. The compounds are not mutagenic. Their action differs from that of a herbicidal active substance and of a fertiliser. The action corresponds more to the effects which can be observed on application of ethylene to various parts of plants. It is known that also the plant itself produces, in various stages of development, ethylene to a varying extent, particularly before and during the ripening process of the fruits, and at the end of the vegetation period as the abscission of the fruit occurs. Since the regulation of fruit ripening and abscission by chemical substances is of the greatest commercial significance for the cultivation of fruit, citrus fruits, pineapples and cotton, compounds have been sought with which such effects might be obtained without damage being caused to the treated plants. Although various classes of substances have become known with which it was possible for certain of these effects, with regard to growth regulation, to be achieved; the sphere of action of these substances in no way corresponds to that of ethylene.

The present invention relates to new agents and processes for the regulation of plant growth by the use of β-halogen-ethyl-silanes as active substances, also to new β-halogen-ethyl-silanes, and to processes for the production of these silanes.

The novel β-halogen-ethyl-silanes contained as active substances in the new agents correspond to formula I:

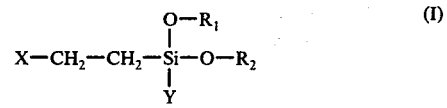

The symbols in this formula have the following meanings: X represents chlorine or bromine, Y represents chlorine or the radical —$OR_3$; $R_1$, $R_2$ and $R_3$ represent, independently of each other, alkyl radicals having 6 to 18 carbon atoms; alkyl radicals substituted by halogen, alkoxy, alkenyloxy, phenoxy, cycloalkyl, alkylthio, alkoxycarbonyl, by a heterocyclic radical and/or di- and trialkylammonio, alkenyl or halogenalkenyl; alkynyl; cycloalkyl; phenyl radicals optionally mono- or polysubstituted by cyano, alkyl, halogenalkyl, alkoxy, alkylthio, and/or alkoxycarbonyl; benzyl radicals optionally mono- or polysubstituted by alkyl, alkoxy and/or halogen; one or more of the symbols $R_1$, $R_2$ and $R_3$ can also represent the group —$CO$-$R_4$ wherein $R_4$ stands for $C_6$-$C_{18}$ alkyl, alkenyl or alkynyl radical; a halogenalkyl or halogenalkenyl radical; an alkyl or alkenyl radical substituted by cycloalkyl or phenyl, whereby phenyl can be substituted by alkyl, alkoxy and/or halogen; an alkoxyalkyl; an alkoxycarbonylalkyl; a phenyl radical optionally substituted by halogen, lower alkyl or lower alkoxy; or a heterocyclic 5- or 6-membered radical, $R_1$ and $R_2$, also with the signification of —$CO$-$R_4$, together with the adjacent atoms, can also form a silicium containing saturated or unsaturated heterocyclic ring system.

By alkyl radicals in formula I, other than when $R_1$, $R_2$, $R_3$ or $R_4$ is unsubstituted alkyl, are meant straight-chain or branched radicals having 1 to 18 carbon atoms, such as, e.g. methyl, ethyl, n-propyl, isopropyl, n-butyl, sec-butyl, n-hexyl, n-octyl, n-dodecyl, n-octadecyl, etc.. Especially the straight-chain and branched alkyl radicals having 1 to 8 carbon atoms form the alkyl substituents or the alkyl moiety of alkoxy, alkylthio, di- and trialkylammonio or alkoxycarbonyl substituents of an alkyl radical or of a phenyl radical. Halogenalkyl radicals are alkyl radicals having 1 to 6 carbon atoms, which can be substituted by fluorine, chlorine and/or bromine, such as, e.g. trifluoromethyl, 2-chloroethyl, 6-chlorohexyl, etc.. By alkenyl radicals are meant, in formula I, straight-chain or branched radicals having 3 to 18 carbon atoms, e.g. propenyl, butenyl, octenyl, decenyl, heptadecenyl radicals. These alkenyl radicals can be mono- or polysubstituted by halogens, such as fluorine, chlorine, bromine and/or iodine. Alkenyl radicals having 3 to 6 carbon atoms form the alkenyl moiety of alkenyloxy radicals. Alkynyl radicals preferably contain 3 to 8 carbon atoms in a straight chain, such as, e.g. 2-propynyl, 2-butynyl or 3-hexynyl. By cycloaliphatic radicals are meant mono- or polycyclic cycloalkyl or cycloalkenyl radicals having 3 to 12 carbon atoms, such as, e.g. cyclopropyl, cyclopentyl, cyclopentenyl, cyclohexyl, cyclohexenyl, bicycloheptyl, etc.

5- or 6-Membered heterocyclic radicals as $R_4$ or as substituents of alkyl radicals $R_1$, $R_2$, $R_3$ may contain 1 or 2 hetero atoms, especially nitrogen and/or oxygen. Heterocyclic ring systems containing the Si-atom and being formed by radicals $R_1$ and $R_2$, including also the type $-COR_4$, may be saturated or unsaturated, the bridging hydrocarbon moiety of $R_1 + R_2$ being an alkylene or alkenylene member. Anions of di- or trialkylammonio radicals (which may be considered as salt forms of a dialkyl amino radical) are e.g. those of hydrogen halides, hydrohalogenic acids, alkyl sulfonic acids, alkyl phosphoric acids, and the like.

Preferred compounds correspond to the formulae $$X-CH_2-CH_2-\underset{\underset{OR_3}{|}}{\overset{\overset{OR_1}{|}}{Si}}-OR_2 \qquad (IA)$$

wherein $R_1$, $R_2$ and $R_3$ are identical and are defined as previously noted; and $$X-CH_2-CH_2-Si-(O-CO-R_4)_3 \qquad (IB)$$

wherein X and $R_4$ are as previously defined.

Particularly preferred compounds of formula IA have $R_1$, $R_2$ and $R_3$ represent alkyl of from 6 to 18 carbon atoms, halogenoalkyl, alkenyl, halogenoalkenyl, alkynyl, alkoxyalkyl, alkylthioalkyl and benzyl optionally substituted by alkyl, alkoxy or halogen; and, furthermore, where $R_1$, $R_2$ and $R_3$ represent alkyl of from 6 to 18 carbon atoms, halogenoalkyl, alkoxyalkyl, and alkylthioalkyl.

The new β-halogen-ethyl-silanes according to the present invention are produced by reaction of a β-halogen-ethyl-trichlor-silane of formula III:

$$X-CH_2-CH_2-Si-(Cl)_3 \qquad (II)$$

with three equivalents of an acid of formula III:

$$R_4-\underset{\underset{O}{\|}}{C}-OH \qquad (III)$$

or of a carboxylic acid anhydride of formula IV:

$$R_4-\underset{\underset{O}{\|}}{C}-O-\underset{\underset{O}{\|}}{C}-R_4 \qquad (IV)$$

to give a compound of formula V:

$$X-CH_2-CH_2-Si-(O-\underset{\underset{O}{\|}}{C}-R_4)_3 \qquad (V);$$

and, optionally, by stepwise exchange of one, two or three of the radicals $$-O-\underset{\underset{O}{\|}}{C}-R_4$$

by radicals of alcohols of the formulae VI, VII, VIII

| | |
|---|---|
| $R_1OH$ | (VI) |
| $R_2OH$ | (VII) |
| $R_3OH$ | (VIII) |

If, in the starting compound of formula II X represents bromine, also low molecular alkanols may be used for the exchange of the radicals $-O-CO-R_4$ in formula V. If no one of the radicals $R_1$, $R_2$ and $R_3$ is identical with $$-\underset{\underset{O}{\|}}{C}-R_4,$$

then the new β-halogen-ethyl-silanes of formulae I can be produced according to a variant of the process by reaction of a β-halogen-ethyl-trichloro-silane of formula II with one, two or three equivalents of one of the alcohols of the formula VI, VII or VIII.

X in formula II represents chlorine or bromine; $R_4$ in formulae III and IV has the meaning given under formula I; and $R_1$, $R_2$ and $R_3$ in formulae VI, VII and VIII have the meaning given under formula I.

As in the reaction according to the invention, the exchange of the 3 chlorine atoms of the starting compound of formula II occurs stepwise, it is clear that intermediates, i.e. dichloro- and monochloro-silanes of formulae $$X-CH_2-CH_2-Si\underset{OR_1}{\overset{Cl_2}{\diagup}} \quad \text{and} \quad X-CH_2-CH_2-Si\underset{OR_2}{\overset{Cl}{\diagup}}-OR_1$$
$$\qquad\qquad (a) \qquad\qquad\qquad\qquad (b)$$

can be isolated during the synthesis or as impurities from the crude final product.

The compounds (b) are embraced by the general formulae I and show also biological, plant growth regulating activity.

The process is preferably carried out in the presence of solvents and/or diluents which are inert to the reactants. Aprotic solvents are particularly suitable, such as, e.g. aliphatic and aromatic hydrocarbons, e.g. hexane, cyclohexane, benzene, toluene, xylene, halogenated hydrocarbons such as chlorinated ethylene, carbon tetrachloride, chloroform, chlorobenzene, also ethers and ethereal compounds such as diethyl ether, tetrahydrofuran, etc..

To obtain a complete reaction, it is also possible for the alcohols, carboxylic acids and carboxylic acid anhydrides employed as reactants to serve, when used in excess, as solvents or diluents.

Furthermore, it can be necessary in some cases to add an acid-binding agent to the reaction mixture. Suitable for this purpose are, in particular, tertiary amines such as trialkylamines, e.g. triethylamine, pyridine and pyridine bases, dialkylanilines, etc..

The reaction temperatures are in the range of 0° to 100° C; the reaction duration can be between a few minutes and several days, and depends to a great extent on the reactivity of the alcohols employed.

The present invention also relates to new compositions containing, as active substances, β-halogen-ethyl-silanes, the said new compositions having a stimulating or retarding effect on plant growth in the various stages of development of the plants. By virtue of the very good stability of the active substances of formula I, these compositions (agents) must not contain, apart from the usual carriers, distributing agents, and stabilisers protecting against the effects of light and oxidation, any additional acid stabilising additive, and have therefore, an unlimited field of application. The vegetative plant growth and the germination power are influenced by the new agents; and the blossom formation, the development of the fruit and the formation of separating tissues promoted. In the case of monocotyledons, an increase in tillering and branching was observed with a simultaneous reduction of growth in height. There was moreover a strengthening of the support tissues of the stalks in the case of the treated plants. The formation or undesirable side shoots is very greatly reduced on various types of plants. Furthermore, gum trees are stimulated to produce a greater latex discharge, an effect which is of great commercial importance. A control of the blossoming time and of the number of blossoms is possible in the case of many ornamental and cultivated plants. This effect is an especially important factor in connection with pineapples. If all the trees or shrubs blossom simultaneously, then the crops can be gathered within a comparatively short space of time. With regard to cucurbitaceae, there occurs a displacement of the blossom sex differentiation in favour of pistillate flowers.

The active substances promote the development of abscission layers, particularly between stalks and petioles. Consequently, fruits of all kinds, e.g. apples, pears, peaches, tomatoes, bananas, prunes, pineapples, cherries, citrus fruits and, particularly oil fruits (olives) can be separated from the fruit stems manually or mechanically without the exertion of great force. It is particularly in the area of olive abscission that the instant compounds excel. Damage to foliage and branches, which results from shaking trees and shrubs or by plucking fruit is largely avoided and production capacity increased. Tests have also shown that in the case of fruit trees, particularly peaches, there occurs a thinning of blossom and fruit.

The extent and the nature of the action are dependent on the most diverse factors, particularly on the time of application with regard to the stage of development of the plant, and on the application concentration. These factors vary, however, depending on the type of plant and on the desired effect. Thus, for example, ornamental plants, of which, e.g. the intensity and number of the blossoms are to be increased, before development of the blossom setting; plants of which the fruit is to be sold, or in some other way utilized, after blossoming or at an appropriate interval of time before the gathering of the crop. Application of the active substances is effected by the use of solid or liquid agents, these being applied to parts of plants above the ground, to the surface of the soil, as well as into the soil itself. The preferred method is the application to the parts of plants above the soil, for which purpose solutions or aqueous suspensions are most suitable. In addition to solutions and dispersions for the treatment of the growth substrate (soil), dusts, granulates and scattering agents are also suitable.

The plant growth regulating action of the new agents can often be positively invluenced by the addition of organic or inorganic acids and bases (e.g. acetic acid or sodium carbonate).

Agents according to the invention are produced in a manner known per se by the intimate mixing and grinding of active substances of the general formula I with suitable carriers, optionally with the addition of dispersing agents or solvents which are inert to the active substances.

Water-dispersible concentrates of active substance, i.e. wettable powders, pastes and emulsion concentrates, are active substance concentrates which can be ciluted with water to obtain any desired concentration. They consist of active substance, carrier, optionally additives which stabilize the active substance, surface-active substances, and anti-foam agents and, optionally, solvents. The concentration of active substance in these agents is 0.5 – 80%.

The wettable powders and pastes are obtained by the mixing and grinding of the active substances with dispersing agents and pulverulent carriers, in suitable devices, until homogeneity is attained. Suitable carriers are, e.g. the following: kaolin, talcum, bole, loess, chalk, limestone, ground limestone, Attaclay, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Suitable dispersing agents are, e.g. the following: condensation products of sulphonated naphthalene and sulphonated naphthalene derivatives with formaldehyde, condensation products of naphthalene or of naphthalene-sulphonic acids with phenol and formaldehyde, as well as alkali, ammonium and alkaline-earth metal salts of ligninsulphonic acid, also alkylarylsulphonates, alkali metal salts and alkaline-earth metal salts of dibutylnaphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary acetylene glycols, dialkyl dilauryl ammonium chloride, and fatty acid alkalimetal and alkaline-earth metal salts.

To these mixtures may also be added additives stabilizing the active substance, and/or non-ionic, anion-oictive and cation-active substances, which, for example, improve the adhesiveness of the active substances on plants and on parts of plants (adhesives and agglutinants), and/or ensure a bettwe wettability (wetting agents). Suitable adhesives are, for example, the following: olein/lime mixture, cellulose derivatives (methyl cellulose, carboxymethyl cellulose), hydroxyethylene glycol ethers of mono- and dialkylphenols having 5 – 15 ethylene oxide radicals per molecule and 8 – 9 carbon atoms in the alkyl radical, ligninsulphonic acid, alkali metal and alkaline-earth metal salts thereof, polyethylene glycol ethers (carbowaxes), fatty alcohol polyglycol ethers having 5 – 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea/formaldehyde, as well as latex products. The active substances are so mixed, ground, sieved and strained with the above-mentioned additives that the solid constituent in the case of wettable powders has a particle size not exceeding 0.02 to 0.04 mm, and in the case of pastes not exceeding 0.03 mm.

Emulsion concentrates and pastes are prepared by application of the dispersing agents such as those mentioned in the preceding paragraphs, organic solvents and water. Suitable solvents are, e.g. the following: ketones, benzene, xylenes, toluene, dimethylsulphoxide, and mineral oil fractions boiling in the range of 120° to 350°. The solvents must be practically odourless, non-phytotoxic, and inert to the active substances.

Furthermore, the agents according to the invention can be employed in the form of solutions. For this purpose, the active substance (or several active substances)

of the general formula I is (or are) dissolved in suitable organic solvents, solvent mixtures, or water. The following can be used as organic solvents: aliphatic and aromatic hydrocarbons, chlorinated derivatives thereof, alkylnaphthalenes, or mineral oils on their own or in admixture with each other. The solutions should contain the active substances in a concentration range of from 1 to 20%.

The solid preparations, such as dusts, scattering agents and granulates, contain aolid carriers such as those mentioned in the foregoing, and, optionally, additives stabilizing the active substance. The particle size of the carriers is for dusts advantageously up to about 0.1 mm; for scattering agents from about 0.075 mm to 0.2 mm; and for granulates 0.2 mm or coarser. The concentrations of active substance in the solid preparations are from 0.5 to 80%.

All the mentioned active substance concentrates may also contain agents stabilizing against the effects of light, and antioxidants.

Granulate

The following substances are used for the preparation of a 5% granulate:
5 parts of 2-chloroethyl-tris-(2'-chloroethoxy)-silane,
0.25 parts of epichlorohydrin,
0.25 parts of cetyl polyglycol ether,
3.50 parts of polyethylene glycol ("carbowax"),
91 parts of kaolin (particle size 0.2 – 0.8 mm).

The active substance is mixed with epichlorohydrin and the mixture dissolved in 6 parts of acetone; to the solution are then added polyethylene glycol and cetyl polyglycol ether. The thus obtained solution is sprayed on to kaolin, and the acetone subsequently evaporated in vacuo.

Wettable powder

The following constituents are used for the preparation of (a) a 40%, (b) a 50%, (c) a 25%, and (d) a 10% wettable powder:
(a) 40 parts of 2-chloroethyl-tris-(octyloxy)-silane,
5 parts of sodium lignin sulphonate,
1 part of sodium dibutyl-naphthalene sulphonate,
54 parts of silicic acid;
(b) 50 parts of 2-chloroethyl-tris-(dodecyloxy)-silane,
5 parts of alkylaryl sulphonate ("Tinovetin B"),
10 parts of calcium lignin sulphonate,
1 part of Champagne chalk/hydroxyethyl cellulose mixture (1 : 1),
20 parts of silicic acid,
14 parts of kaolin;
(c) 25 parts of 2-chloroethyl-tris-(4'-methoxy-benzoxy)-silane,
5 parts of the sodium salt of oleylmethyl tauride,
2.5 parts of naphthalenesulphonic acid/formaldehyde condensate,
0.5 parts of carboxymethyl cellulose,
5 parts of neutral potassium aluminium silicate,
62 parts of kaolin;
(d) 10 parts of 2-chloroethyl-tris-(4'-chlorobenzoxy)-silane,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; the mixture is subsequently ground in suitable mills and rollers. Wettable powders are thus obtained which can be diluted with water to give suspensions of any desired concentration.

Emulsion Concentrate

The following constituents are mixed together to produce 25% emulsion concentrates:
(a) 25 parts of 2-chloroethyl-tris-(benzoxy)-silane,
5 parts of a mixture of nonylphenolpolyoxyethylene and calcium-dodecylbenzene sulphonate,
70 parts of xylene;
(b) 25 parts of 2-chloroethyl-tris-(2'-chloroethoxy)-silane,
10 parts of a mixture of nonylphenolpolyoxyethylene and calcium-dodecylbenzene sulphonate,
65 parts of cyclohexanone.

This concentrate can be diluted with water to obtain emulsions of any desired concentration. Such emulsions are suitable for the thinning out of blossom and fruit, for the accelerated ripening of fruits, and for the promotion of fruit and leaf abscission.

The following examples serve to illustrate the preparation of the compounds of this invention. Listed in the attached tables are further new $\beta$-halogen-ethylsilanes of formulae I and II produced in the manner described in the examples.

The temperatures are given in the examples in degrees Centigrade, and the pressure in Torr.

EXAMPLE 1

(a) An amount of 40.8 g of 2-chloroethyl-trichlorosilane is dissolved in 71.5 g of acetic acid anhydride, and the solution allowed to stand at room temperature for 21 hours in a closed vessel. The reaction product is concentrated in vacuo to obtain 44.6 g of 2-chloroethyl-tris-(acetyloxy)-silane, B.P.: 85° – 88°/0.1 Torr, $n_D^{20} = 1.6687$. b) An amount of 26.9 g of 2-chloroethyl-tris-(acetyloxy)silane is dissolved in 40 ml of absolute benzene. To the solution are added at 50° – 55°, within 60 minutes, 10.8 g of benzyl alcohol in 20 ml of absolute benzene. Stirring is carried out for 4½ hours at 50° – 55°. The reaction mixture is concentrated in vacuo, and 14.3 g of 2-chloroethyl-(benzyloxy-diacetyloxy)-silane are obtained, B.P.: 125 – 127°/0.001 Torr, $n_D^{20} = 1.4840$. (Compound 1).

|  | Calculated | Found |
| --- | --- | --- |
| C | 49.3 | 49.4 |
| H | 5.4 | 5.4 |
| Cl | 11.2 | 11.7 |
| Si | 8.9 | 8.9 |

EXAMPLE 2

An amount of 26.9 g of 2-chloroethyl-tris-(acetyloxy)silane, obtained according to example 1a, is dissolved in 40 ml of absolute benzene; to this solution are then added at 50 – 55°, within 60 minutes, 21.6 g of benzyl alcohol in 20 ml of absolute benzene. Stirring is carried out for 4½ hours at 50° – 55°. The reaction mixture is concentrated in vacuo to obtain 20.2 g of 2-chloroethyl-(dibenzyloxy)-acetyloxy)-silane, B.P.: 164 – 166°/0.005 Torr, $n_D^{25} = 1.5218$. (Compound 2).

|  | Calculated | Found |
| --- | --- | --- |
| C | 59.3 | 59.4 |
| H | 5.8 | 5.6 |

-continued

|    | Calculated | Found |
|----|------------|-------|
| Cl | 9.7        | 10.2  |
| Si | 7.7        | 8.0   |

EXAMPLE 3

An amount of 10.5 g of 2-chloroethyl-trichlorosilane is dissolved in 150 ml of absolute diethyl ether; to this solution are then added at −5° to −10°, within 5 minutes, 22.7 g of 4-chlorobenzyl alcohol, and following this, in the course of 30 minutes, 12.6 g of absolute pyridine dissolved in 50 ml of absolute ether. Stirring is carried out for a further hour at 0°, and the mixture then refluxed for 18 hours.

The reaction mixture is filtered, the filtrate washed twice with water, dried, and concentrated in vacuo. In this manner are obtained 23.5 g of 2-chloroethyl-tris(4'-chlorobenzoxy)-silane, B.P.: 200° – 210°/0.01 Torr, $n_{20}^D = 1.5636$. (Compound 3).

|    | Calculated | Found |
|----|------------|-------|
| C  | 53.5       | 53.4  |
| H  | 4.3        | 4.3   |
| Cl | 27.5       | 27.8  |
| Si | 5.4        | 5.6   |

EXAMPLE 4

An amount of 16.9 g of 3-chlorobuten-(2)-ol is dissolved in 150 ml of absolute diethyl ether. The solution is cooled to −10° to −5° and 12.6 g of absolute pyridine are added; at the same temperature is then added dropwise, within one hour, a solution of 10.5 g of 2-chloroethyltrichlorosilane in 50 ml of absolute diethyl ether. The mixture is stirred for one hour at 0°, for 2 hours at room temperature, and for 18 hours with refluxing. The reaction mixture is afterwards filtered, the filtrate quickly washed with ice-cold water, dried, and concentrated in vacuo. Thus obtained are 21.5 g of 2-chloroethyltris-[3'-chlorobutenyl-(2')-oxy]-silane, B.P.: 145° – 150°/0.05 Torr, $n_{20}^D = 1.4912$. (Compound 4).

|    | Calculated | Found |
|----|------------|-------|
| C  | 41.2       | 41.6  |
| H  | 5.4        | 5.4   |
| Cl | 34.8       | 34.9  |
| Si | 6.9        | 6.6   |

EXAMPLE 5 (PRODUCTION OF AN INTERMEDIARY PRODUCT)

An amount of 59,4 g of 2-chloroethyl-trichloro-silane is dissolved in 750 ml of absolute diethylether. To the obtained solution is then added at −5° to −10°, within 1 hour, a solution of 34,9 g of hexanol-(1) and 23,7 g of absolute pyridine in 250 ml of absolute diethylether. The mixture is then stirred for 12 hours at room temperature, filtered and the filtrate concentrated by evaporation in vacuo. After fractionated distillation, 39,2 g of 2-chloroethyl-(hexyloxy-dichloro)silane are obtained; B.P.: 69°–72°/0,1 Torr.

|   | Calculated | Found |
|---|------------|-------|
| C | 36.5       | 36.3  |
| H | 6.5        | 6.5   |

-continued

|    | Calculated | Found |
|----|------------|-------|
| Si | 10.7       | 11.0  |

EXAMPLE 6

An amount of 59,4 g of 2-chloroethyl-trichloro-silane is dissolved in 750 ml of absolute diethylether. To the obtained solution is then added at −5° to −10°, within 1 hour, a solution of 69,7 g hexanol-(1) and 47,5 g absolute pyridine in 250 ml of absolute diethylether. The mixture is then stirred for 12 hours at room temperature, filtered and the filtrate concentrated by evaporation in vacuo. After fractionated distillation, 32,5 g of 2-chloro-(dihexyloxy-chloro)silane are obtained; B.P.: 97°–102°/0.001 Torr; $n_D^{20} = 1.4423$. (Compound 5).

Table I

Compounds of formula $$X-CH_2-CH_2-Si\begin{matrix}O-R_1\\O-R_2\\O-R_3\end{matrix}$$

| No. | $R_1=R_2=R_3$ | X | Physical data M.P.; B.P./Torr; $n_D$ |
|-----|---------------|---|--------------------------------------|
| 6   | Hexyl         | Br | B.P.: 145–50°/0,01 |
| 7   | 2-Ethyl-hexyl | Cl | $n_D^{20} = 1,4480$ |
| 8   | Octyl         | Cl | B.P.: 165–70°/0,001 |
| 9   | Octyl         | Br | B.P.: 165–70° 10,005 |
| 10  | Dodecyl       | Cl | $n_D^{20} = 1,4545$ |
| 11  | Dodecyl       | Br | $n_D^{20} = 1,4582$ |
| 12  | Octadecyl     | Cl | M.P.: 33–36° |
| 13  | Octadecyl     | Br | M.P.: 35–36° |
| 14  | 2-Chloroethyl | Cl | B.P.: 123–26°/0,001 |
| 15  | 2-Chloropropyl | Cl | B.P.: 128°/0,001 |
| 16  | 6-Chlorohexyl | Cl | B.P.: 210–15°/0,03 |
| 17  | 2-Methoxyethyl | Cl | B.P.: 103–105°/0,05 |
| 18  | 2-Ethoxyethyl | Cl | B.P.: 122–125°/0,005 |
| 19  | 2-Ethoxyethyl | Br | B.P.: 173°/0,001 |
| 20  | 2-Butyloxyethyl | Cl | $n_D^{20} = 1,4495$ |
| 21  | 2-Allyloxyethyl | Cl | B.P.: 140–145°/0,001 |
| 22  | 2-Ethylthioethyl | Cl | B.P.: 195–200°/0,005 |
| 23  | 2-Octylthioethyl | Cl | $n_D^{20} = 1,4895$ |
| 24  | 3-Phenylpropyl | Cl | $n_D^{20} = 1,5340$ |
| 25  | 2-Phenoxyethyl | Cl | $n_D^{20} = 1,5466$ |
| 26  | 2-Propenyl    | Cl | B.P.: 95–100°/0,2 |
| 27  | 2-Butenyl     | Cl | B.P.: 110–15°/0,2 |
| 28  | 2-Butenyl     | Br | B.P.: 115–20°/0,01 |
| 29  | 3,7-Dimethyl-2-octenyl | Cl | $n_D^{20} = 1,4707$ |
| 30  | 2-Propinyl    | Cl | B.P.: 94°/0,35 |
| 31  | 2-Propinyl    | Br | B.P.: 115–20°/0,005 |
| 32  | 3-Hexinyl     | Cl | B.P.: 170–5°/0,005 |
| 33  | 3-Chloro-2-butenyl | Cl | B.P.: 145–50°/0,005 |
| 34  | 3-Phenyl-2-propenyl | Cl | $n_D^{20} = 1,5832$ |
| 35  | 3-Phenyl-2-propenyl | Br | $n_D^{20} = 1,5882$ |
| 36  | 3-Cyanoethyl  | Cl | $n_D^{20} = 1,4696$ |
| 37  | Ethoxycarbonyl-methyl | Cl | $n_D^{20} = 1,4496$ |
| 38  | 1-Ethoxycarbonyl-(1-methyl)-methyl | Cl | B.P.: 154–158°/0,3 |
| 39  | Butoxycarbonyl-methyl | Cl | $n_D^{20} = 1,4480$ |
| 40  | Cyclohexyl    | Cl | B.P.: 165–170°/0,001 |
| 41  | Cyclohexylmethyl | Cl | B.P.: 180–190°/0,001 |
| 42  | Cyclohexylmethyl | Br | $n_D^{20} = 1,4833$ |
| 43  | Benzyl        | Cl | B.P.: 190–200°/0,001 |
| 44  | Benzyl        | Br | $n_D^{20} = 1,5612$ |
| 45  | 4-Chlorobenzyl | Cl | B.P.: 200–20°/0,01 |
| 46  | 4-Chlorobenzyl | Br | $n_D^{20} = 1,5757$ |
| 47  | 4-Methoxybenzyl | Cl | $n_D^{20} = 1,5224$ |
| 48  | 2,4-Dichlorobenzyl | Cl | $n_D^{20} = 1,6637$ |
| 49  | 4-Methylbenzyl | Cl | $n_D^{20} = 1,5433$ |
| 50  | Phenyl        | Cl | $n_D^{20} = 1,5623$ |
| 51  | 4-Chlorophenyl | Cl | $n_D^{20} = 1,5769$ |
| 52  | 3-Chlorophenyl | Cl | $n_D^{27} = 1,5262$ |
| 53  | 3,4-Dichlorophenyl | Cl | $n_D^{27} = 1,5257$ |
| 54  | 3,5-Dichlorophenyl | Cl | $n_D^{27} = 1,5268$ |
| 55  | 4-Bromophenyl | Cl | $n_D^{27} = 1,5418$ |
| 56  | 4-Methoxyphenyl | Cl | $n_D^{20} = 1,5620$ |
| 57  | 4-Methoxylphenyl | Br | $n_D^{20} = 1,5641$ |
| 58  | 3-Methoxyphenyl | Cl | $n_D^{20} = 1,5590$ |
| 59  | 4-Butyloxyphenyl | Cl | $n_D^{20} = 1,5307$ |
| 60  | 4-tert-Butylphenyl | Cl | M.P.: 75–77° |

Table I-continued

Compounds of formula $$X-CH_2-CH_2-Si\begin{matrix}O-R_1\\O-R_2\\O-R_3\end{matrix}$$

| No. | $R_1=R_2=R_3$ | X | Physical data M.P.; B.P./Torr; $n_D$ |
|---|---|---|---|
| 61 | 3-Methylphenyl | Cl | $n_D^{27} = 1,5385$ |
| 62 | 3-Methylphenyl | Br | $n_D^{20} = 1,5490$ |
| 63 | 3,4-Dimethylphenyl | Cl | $n_D^{27} = 1,4935$ |
| 64 | 3-Formylphenyl | Cl | M.P.: 98–101° |
| 65 | 4-Cyanophenyl | Cl | M.P.: 106–111° |
| 66 | 4-Ethoxycarbonylphenyl | Cl | M.P.: 112–114° |
| 67 | 3-Ethoxycarbonylphenyl | Cl | M.P.: 65–70° |
| 68 | tetrahydropyranylmethyl (O-ring with CH₂–) | Cl | B.P.: 195–200° /0,001 |
| 69 | dihydrofuranylmethyl (O-ring with CH₂–) | Cl | B.P.: 152–154° /0,001 |
| 70 | thiophenylmethyl (S-ring with CH₂–) | Cl | $n_D^{23} = 1,5771$ |
| 71 | tetrahydrofuranylmethyl (O-ring with CH₂–) | Cl | $n_D^{25} = 1,4727$ |

Table II

| No. | $R_1=R_2=R_3 = -CO-R_4$ $R_4$ is: | X | Physical data |
|---|---|---|---|
| 72 | Undecyl | Cl | M.P.: 42–44° |
| 73 | Undecyl | Br | M.P.: 44–47° |
| 74 | Heptadecyl | Cl | M.P.: 54–57° |
| 75 | 2-Propenyl | Cl | $n_D^{20} = 1,4484$ |
| 76 | 1-Propenyl | Cl | M.P.: 24–27° |
| 77 | 2-Propenyl | Br | $n_D^{20} = 1,4621$ |
| 78 | 9-Decenyl | Cl | $n_D^{20} = 1,4480$ |
| 79 | 8,11-Heptadecadienyl | Cl | $n_D^{20} = 1,4705$ |
| 80 | 2-Chloroethyl | Cl | $n_D^{20} = 1,4681$ |
| 81 | 1-Bromopentyl | Cl | $n_D^{20} = 1,4513$ |
| 82 | 10-Bromodecyl | Cl | M.P.: 49–50° |
| 83 | 10-Bromodecyl | Br | M.P.: 48–50° |
| 84 | cis-2-Chloroethenyl | Cl | M.P.: 25° |
| 85 | cis-2-Chloroethynyl | Br | M.P.: 55–58° |
| 86 | Phenylmethyl | Cl | M.P.: 74–78° |
| 87 | Phenylmethyl | Br | M.P.: 20–30° |
| 88 | 2-Phenylethyl | Cl | M.P.: 35–39° |
| 89 | 4-Chlorphenylmethyl | Cl | M.P.: 99–103° |
| 90 | 2-Methylphenylmethyl | Cl | M.P.: 57–60° |
| 91 | 3-(4'-Methoxyphenyl)-ethyl | Cl | M.P.: 98–102° |
| 92 | 4-Ethoxycarbonylbutyl | Cl | |
| 93 | 3-Oxobutyl | Cl | $n_D^{20} = 1,4590$ |
| 94 | 3-Oxobutyl | Br | $n_D^{20} = 1,4841$ |
| 95 | 5-Phenyl-5-oxo-pentyl | Cl | M.P.: 73–75° |
| 96 | 2-Ethoxyethyl | Cl | $n_D^{20} = 1,4365$ |
| 97 | 3-Phenoxypropyl | Cl | M.P.: 58–60° |
| 98 | 2,4-Dichlorophenoxymethyl | Cl | M.P.: 140° |
| 99 | 2,4-Dichlorophenoxymethyl | Br | M.P.: 137–138° |
| 100 | 2-(4'-Chlorphenyl)-1-ethenyl | Cl | |
| 101 | 2-Phenyl-1-ethenyl | Cl | M.P.: 128–130° |
| 102 | 2-Phenyl-1-ethenyl | Br | M.P.: 129–131° |
| 103 | 2-(3',4'-Dichlorphenyl)-1-ethenyl | Cl | M.P.: >235° |
| 104 | 2-(4'-Methoxyphenyl-1-ethenyl | Cl | M.P.: 178° |

Table II-continued

| No. | $R_1=R_2=R_3 = -CO-R_4$ $R_4$ is: | X | Physical data |
|---|---|---|---|
| 105 | Cyclohexylmethyl | Cl | $n_D^{20} = 1,4494$ |
| 106 | Cyclohexylmethyl | Br | $n_D^{20} = 1,4592$ |
| 107 | Cyclohexyl | Cl | $n_D^{20} = 1,4578$ |
| 108 | Cyclopropyl | Cl | $n_D^{20} = 1,4515$ |
| 109 | 3-Cyclohexenyl | Cl | $n_D^{20} = 1,4740$ |
| 110 | 3-Cyclohexenyl | Br | $n_D^{20} = 1,4807$ |
| 111 | 2-Cyclopentenyl | Cl | $n_D^{20} = 1,4680$ |
| 112 | 2-Cyclopentenyl | Br | |
| 113 | Phenyl | Cl | $n_D^{20} = 1,5632$ |
| 114 | 4-Chlorophenyl | Br | M.P.: 233° |
| 115 | 4-Methoxy-phenyl | Br | M.P.: 177–178° |
| 116 | 4-Methylphenyl | Cl | M.P.: 165–170° |
| 117 | pyridyl | Br | |
| 118 | furanyl | Br | M.P.: 123–126° |
| 119 | thienyl | Br | M.P.: 123–125° |
| 120 | pyrazinyl | Cl | |

Table III

| No. | $R_1$ | $R_2$ | $R_3 = CO-R_4$ is: | X | Physical data |
|---|---|---|---|---|---|
| 121 | Benzyl | $= R_3$ | Methyl | Cl | B.P.: 126–27° /0,001 |
| 122 | Benzyl | $= R_3$ | Methyl | Br | B.P.: 140–143° /0,01 |
| 123 | Benzyl | Benzyl | Methyl | Cl | B.P.: 164–166° /0,005 |
| 124 | Octyl | $= R_3$ | Methyl | Cl | B.P.: 115–120° /0,02 |
| 125 | Octyl | Octyl | Methyl | Cl | B.P.: 150–152° /0,005 |
| 126 | 2-Butynyl | 2-Butynyl | Methyl | Cl | |
| 127 | 2-Butenyl | 2-Butenyl | Methyl | Cl | B.P.: 94–98° /0,001 |
| 128 | 4-Chlorbenzyl | $= R_3$ | Ethyl | Cl | $n_D^{20} = 1,4940$ |
| 129 | 4-Chlorbenzyl | $= R_3$ | Ethyl | Br | $n_D^{20} = 1,5042$ |
| 130 | 3,7-Dimethyl-7-octenyl | $= R_3$ | Ethyl | Cl | $n_D^{20} = 1,4525$ |
| 131 | 4-Methoxybenzyl | $= R_3$ | Ethyl | Cl | $n_D^{20} = 1,4890$ |

Table IV

| No. | $R_1$ | $R_2$ | $R_3$ | X | anion | physical data |
|---|---|---|---|---|---|---|
| 132 | $(CH_3)_2\overset{\oplus}{N}(H)-CH_2-CH_2-$ | Hexyl | Hexyl | Cl | Cl$^\ominus$ | M.P.: 25–35° |
| 133 | $(CH_3)_2\overset{\oplus}{N}(H)-CH_2-CH_2-$ | Benzyl | Benzyl | Cl | Cl$^\ominus$ | $n_D^{20} = 1,5212$ |

Table V (Compounds wherein $R_1$ and $R_2$, together with the adjacent atoms form a Si-containing heterocyclic ring system).

| No. | active substance | Physical data |
|---|---|---|
| 134 | $\begin{matrix}CH_3\\ \phantom{X}\diagdown\\ \phantom{XX}C\\ \phantom{X}\diagup\\ CH_3\end{matrix}\begin{matrix}CH_2-O\\ \phantom{XXX}\diagdown\\ \phantom{XXXX}Si-CH_2-CH_2-Cl\\ \phantom{XXX}\diagup\\ CH_2-O\phantom{X}OC_6H_{13}\end{matrix}$ | B.P.: 115–120°/ 0,005 |

Table V-continued (Compounds wherein $R_1$ and $R_2$, together with the adjacent atoms form a Si-containing heterocyclic ring system).

| No. | active substance | Physical data |
|---|---|---|
| 135 | (structure: benzene ring with CH₂–O–Si(OC₂H₅)–O– ring, Si–CH₂–CH₂–Cl) | $n_D^{25} = 1.5233$ |
| 136 | (structure: benzene-1,2-di(CO–O) Si(OC₅H₁₁) ring, Si–CH₂–CH₂–Cl) | $n_D^{20} = 1.4718$ |
| 137 | (structure: CH=CH with two CO–O groups forming ring with Si(OC₅H₁₁), Si–CH₂–CH₂–Cl) | $n_D^{20} = 1.4537$ |
| 138 | (structure: –(CH₂)– with two CO–O groups forming ring with Si(OC₆H₁₃), Si–CH₂–CH₂–Cl) | $n_D^{20} = 1.4400$ |
| 139 | (structure: CO–O and –O– forming ring with Si(OC₆H₁₃), Si–CH₂–CH₂–Cl) | $n_D^{20} = 1.4502$ |

Performance Characteristics Orange Abscission

It was determined in the case of citrus fruits — oranges — that the abscission of fruit is appreciably easier after application of the active substances of formula I. Various active substances were sprayed, in the form of solutions in concentrations of 0.2% – 0.4%, on to branches, well hung with fruit, of various orange trees. The tests were evaluated after 14 days according to the method developed by W. C. Wilson and C. H. Hendershott, cp. Proc. Am. Soc. Hort. Sc. 90, 123–129 (1967). The test consists of measuring the force in kg required for the abscission of the fruit.

| Active substance: | Concentration | Force (kg) |
|---|---|---|
| 8 | 0.2% | 3.7 |
|   | 0.4% | * |
| 43 | 0.2% | * |
|   | 0.4% | * |
| 10 | 0.2% | 4.7 |
|   | 0.4% | 1.1 |
| Control |   | 8.6 |

*The fruit hanging on the tree could be so easily detached that no measurement was possible.

Equally good and significant results were obtained using agents containing the following compounds:
2-chloroethyl-tris-(2'-chloroethoxy)-silane,
2-chloroethyl-tris-[butenyl-(2')-oxy]-silane,
2-chloroethyl-tris-[propenyl-(2')-oxy]-silane,
2-chloroethyl-tris-[3'-chlorobutenyl-(2')-oxy]-silane,
2-chloroethyl-tris-(octadecyloxy)-silane,
2-chloroethyl-tris-[butynyl-(2')-oxy]-silane,
2-chloroethyl-tris-[hexynyl-(3')-oxy]-silane,
2-chloroethyl-tris-(6'-chlorohexyloxy)-silane,
2-chloroethyl-tris-(4'-methoxy-benzoxy)-silane,
2-chloroethyl-tris-(2',4'-dichlorobenzoxy)-silane,
2-chloroethyl-tris-(4'-chlorobenzoxy)-silane.

Apple and Prune Abscission

A similar test procedure was conducted on apples and prunes by neasuring the force in ounces required for the abscission thereof.

| Active Substance | Concentration (ppm) | Pull Force (oz.) |
|---|---|---|
| Apples | | |
| 17 | 500 | 91.2 |
| 17 | 1000 | 16.80 |
| 17 | 2000 | 11.84 |
| 17 | 4000 | 35.36 |
| Control | — | 106.88 |
| Prunes | | |
| 17 | 2000 | 30.75 |
| Control | — | 49.7 |

Tomato Ripening

Tomato plants of the variety "Fournaise" were cultivated outdoors under plastic sheets. After reaching a height of 1.5 m., the shoot tips of the plants were cut away. As the first fruits turn red the plants were sprayed with aqueous preparations formulated from emulsion concentrates of the under-mentioned active substances. Four plants were each treated with 1.5 l of a spray containing 2000 or 4000 ppm of active substance (ppm = parts active substance per million parts of solution). 10, 14 and 17 days after treatment the ripe fruits on the three lowest umbels were harvested.

The sum of the yields (tomatoes) thus obtained is given in the following table:

| Active substance | quantity employed (ppm) | Yield of ripe fruits from the ghree harvests | |
|---|---|---|---|
| | | weight in kg | % of total harvest |
| 8 | 2000 | 4.05 | 61.2 |
|   | 4000 | 5.76 | 71.5 |
| 43 | 2000 | 5.66 | 73.7 |
|   | 4000 | 6.26 | 75.9 |
| 33 | 2000 | 5.92 | 85.2 |
|   | 4000 | 6.50 | 84.3 |
| 27 | 2000 | 5.03 | 63.4 |
|   | 4000 | 6.06 | 75.3 |
| 47 | 2000 | 5.50 | 70.6 |
|   | 4000 | 7.30 | 87.7 |
| 45 | 2000 | 3.37 | 62.9 |
|   | 4000 | 6.80 | 82.4 |
| 32 | 2000 | 5.32 | 77.7 |
|   | 4000 | 5.94 | 85.2 |
| untreated control |   | 3.41 | 52.0 |

Immersion test with plucked green greenhouse tomatoes of the variety "Hybrid".

The active substances were prepared, in a concentration of 1000 and 2000 ppm, as an aqueous liquor with an addition of wetting agent. Each test was carried out with 2 liters of this liquor and 40 unripe picked tomatoes, the procedure being that the tomatoes were immersed for 1 minute in the liquor, and then stored in an air-conditioned room with 70% rel. humidity and at 20° C, with a daily 10-hours' exposure to light (20,000) Lux). Relative degree of ripeness was determined after a period of seven days.

| Active Substance | Concentration (ppm) | Number of Tomatoes | | | | |
|---|---|---|---|---|---|---|
| | | Green | Breaking | Pink | Orange | Red |
| 17 | 1000 | 2 | 6 | 9 | 12 | 11 |
| 17 | 2000 | 3 | 4 | 5 | 10 | 16 |
| Untreated | — | 7 | 3 | 10 | 11 | 9 |

-continued

| Active Substance | Concentration (ppm) | Number of Tomatoes | | | | |
|---|---|---|---|---|---|---|
| | | Green | Breaking | Pink | Orange | Red |
| Control | | | | | | |

Latex Discharge

The resin flow comparable with the latex discharge of gum trees was evaluated with damson trees in the following manner:

Segments of the bark were cut out from the boughs of 12 year old damson trees (*Prunus domestica*). A 10% active substance solution (10 parts active substance, 20 parts xylene, 70 parts castor oil) was then applied to the undamaged surface of the boughs just above and below the above-mentioned incisions, each treatment being repeated on 4 different trees.

Four weeks after said treatment the exuded resin was removed and weighed. The following table gives the average weight of collected resin per treated bough in grams.

| Active substance | Grams resin |
|---|---|
| 56 | 1.81 |
| 31 | 0.53 |
| 45 | 0.52 |
| 32 | 0.85 |
| control (untreated) | 0 |

Peach Thinning

Peach trees, or branches thereof, the variety "Elberta" and "Fay Elberta" were sprayed, subsequent to blossom fall, with aqueous compositions of varying concentrations of active substance. At the time of application, the young fruit was counted. Count was also taken at varying intervals thereafter to determine the amount of remaining fruit. In addition, the remaining fruit was categorized into size with "E" representing the smallest, most undesirable fruit, "A" the largest fruit and "B" the most desirable, marketable fruit.

| Fay Elberta Peaches (Branch Test) | | | | | | | |
|---|---|---|---|---|---|---|---|
| Compound | Rate (ppm) | % Fruit Remaining (56 Days) | Average No. Per Size Category | | | | |
| | | | A | B | C | D | E |
| 17 | 1000 | 38 | — | — | — | — | — |
| 17 | 1500 | 45 | — | — | — | — | — |
| 17 | 2000 | 19 | 0 | 11 | 11 | 0 | 0 |
| 22 | 1000 | 30 | 3 | 10 | 21 | 4 | 0 |
| 22 | 1500 | 26 | 0 | 18 | 7 | 1 | 0 |
| 22 | 2000 | 19 | 4 | 13 | 4 | 0 | 0 |
| Fay Elberta Peaches (Whole Tree Test) | | | | | | | |
| 17 | 1000 | 44 | — | — | — | — | — |
| 17 | 1500 | 29 | — | — | — | — | — |
| 17 | 2000 | 34 | 2 | 17 | 18 | 3 | 0 |
| Control | — | 54 | 0 | 1 | 13 | 15 | 7 |

| Elberta Peaches (Branch Test) | | |
|---|---|---|
| Compound | Rate (ppm) | % Fruit Drop (28 days) |
| 17 | 1000 | 76 |
| 17 | 1500 | 86 |
| 17 | 2000 | 90 |
| 22 | 1000 | 99 |
| 22 | 1500 | 98 |
| 22 | 2000 | 100 |
| Control | — | 76 |

Olive Abscission

On olive trees of the varieties "Coratine", "Zorzalena" and "Hojiblanca", a large number of branches were sprayed, about 1 week before the expected harvest of the olives, with aqueous compositions of the listed active ingredients. The concentration of the active ingredients in the spary liquid was always 2000 ppm. On each tree, some branches were not treated and served as control branches. The tests were evaluated 4 to 14 days after treatment, by uniformly shaking the treated and untreated branches by hand. The olives which fell were counted, the results given in the following table indicating the percent of fallen olives with respect to the initial number of olives on the corresponding branches.

Similar test procedures were also conducted utilizing the following prior art compounds of the aforementioned Leasure patents.

A-bromoethyl-dimethoxy-methyl silane
B-chloromethyl-dimethoxy-methyl silane
C-chloromethyl-diethoxy-methyl silane
D-chloromethyl-diisopropoxy-methyl silane
E-alpha-chloroethyl-dimethoxy-methyl silane

| Compound No. | Olive-fall (%) | Compound | Olive-fall(%) |
|---|---|---|---|
| untreated control | | D | 5% |
| A | 2% | E | 10% |
| B | 2% | 6 | 99% |
| C | 3% | 8 | 96% |
| 10 | 55% | 54 | 29% |
| 15 | 90% | 55 | 36% |
| 17 | 85% | 56 | 81% |
| 18 | 94% | 58 | 30% |
| 19 | 90% | 59 | 60% |
| 20 | 90% | 60 | 52% |
| 21 | 72% | 61 | 74% |
| 22 | 80% | 63 | 28% |
| 23 | 60% | 65 | 26% |
| 24 | 95% | 68 | 88% |
| 25 | 95% | 70 | 33% |
| 26 | 83% | 71 | 80% |
| 28 | 51% | 73 | 25% |
| 29 | 36% | 74 | 34% |
| 30 | 70% | 76 | 38% |
| 31 | 52% | 77 | 98% |
| 32 | 99% | 80 | 48% |
| 33 | 78% | 83 | 38% |
| 36 | 28% | 85 | 31% |
| 37 | 48% | 87 | 66% |
| 41 | 43% | 88 | 34% |
| 43 | 80% | 89 | 41% |
| 44 | 72% | 91 | 41% |
| 45 | 90% | 93 | 30% |
| 46 | 62% | 96 | 44% |
| 47 | 70% | 98 | 42% |
| 48 | 95% | 102 | 43% |
| 49 | 55% | 107 | 24% |
| 50 | 28% | 108 | 28% |
| 52 | 33% | 123 | 33% |
| 124 | 82% | | |
| 125 | 73% | | |
| 127 | 100% | | |
| 129 | 29% | | |
| 130 | 42% | | |
| 131 | 64% | | |
| 132 | 55% | | |
| 133 | 46% | | |
| 134 | 97% | | |
| 135 | 96% | | |

The data presented hereinabove clearly illustrates the excellent growth regulatory performance characteristics of the compounds of this invention. Furthermore, it establishes a distinct pattern of superior performance over the prior art Leasure compounds.

What is claimed is:

1. A beta-halogen-ethyl silane corresponding to the formula

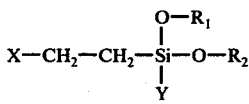

wherein
- X represents chlorine or bromine, Y represents chlorine or the radical —$OR_3$; $R_1$, $R_2$ and $R_3$ represent, independently of each other, alkyl radicals having 6 to 18 carbon atoms; alkyl radicals substituted by halogen, alkenyloxy, phenoxy, cycloalkyl, alkylthio, alkoxycarbonyl, or di- and trialkylammonio, alkenyl or halogenalkenyl; alkynyl; cycloalkyl; phenyl radicals optionally mono- or polysubstituted by cyano, alkyl, halogenalkyl, alkoxy alkylthio, or alkoxycarbonyl; benzyl radicals optionally mono- or polysubstituted by alkyl, alkoxy or halogen; one or more of the symbols $R_1$, $R_2$ and $R_3$ can also represent the group —CO—$R_4$ wherein $R_4$ stands for $C_6$–$C_{18}$ alkyl, alkenyl or alkynyl radical; a halogenalkyl or halogenalkenyl radical; an alkyl or alkenyl radical substituted by cycloalkyl or phenyl, whereby phenyl can be substituted by alkyl, alkoxy or halogen; an alkoxyalkyl; an alkoxycarbonylalkyl; a phenyl radical optionally substituted by halogen, lower alkyl or lower alkoxy.

2. The silane compound of claim 1, wherein Y is $OR_3$.

3. The silane compound of claim 2, wherein
- X represents chlorine or bromine; and each of $R_1$, $R_2$, $R_3$ represents unsubstituted alkyl of from 6 to 18 carbon atoms; $C_1$–$C_{18}$ alkyl substituted by chlorine, bromine, $C_3$–$C_6$ alkenyloxy, phenoxy, $C_3$–$C_{12}$ cycloalkyl, and $C_1$–$C_8$ alkylthio, $C_3$–$C_{18}$ alkenyl; $C_3$–$C_8$ alkynyl; $C_3$–$C_{12}$ cycloalkyl; phenyl; phenyl substituted by alkyl of from 1 to 4 carbon atoms, chlorine, bromine, $C_1$–$C_6$ fluoro-, chloro-, bromoalkyl, alkoxy of from 1 to 4 carbon atoms, and alkylthio of from 1 to 8 carbon atoms, benzyl; and benzyl substituted by alkyl of from 1 to 4 carbon atoms, alkoxy of from 1 to 4 carbon atoms, chlorine and bromine.

4. The silane compound of claim 3, wherein
- $R_1$, $R_2$ and $R_3$ are the same and represent unsubstituted alkyl of from 6 to 18 carbon atoms; $C_1$–$C_6$ fluoro-, chloro-, bromo-alkyl; $C_3$–$C_{18}$ alkenyl; $C_3$–$C_{18}$ fluoro-, chloro-, bromoalkenyl; $C_3$–$C_8$ alkinyl, or benzyl optionally substituted by alkyl of from 1 to 4 carbon atoms, alkoxy of from 1 to 4 carbon atoms, chlorine and bromine.

5. The silane compound of claim 4, wherein X is chlorine and the groups $R_1$, $R_2$ and $R_3$ represent $C_6$–$C_{18}$ unsubstituted alkyl.

6. The silane compound of claim 3, wherein X is bromine.

7. The silane compound of claim 3, wherein $R_1$, $R_2$ and $R_3$ are the same and represent $C_6$–$C_{18}$ unsubstituted alkyl, $C_1$–$C_6$ fluoro-chloro-bromo-alkyl and $C_1$–$C_{18}$ alkyl substituted by $C_1$–$C_8$ alkylthio.

8. The silane compound of claim 7, wherein $R_1$, $R_2$ and $R_3$ are alkylthioalkyl.

9. The silane compound of claim 8, wherein $R_1$, $R_2$ and $R_3$ are 2-ethylthioethyl.

10. The silane compound of claim 4, wherein $R_1$, $R_2$ and $R_3$ are benzyl or benzyl substituted by $C_1$–$C_4$ alkoxy, chlorine or bromine.

11. The silane compound of claim 10, wherein $R_1$, $R_2$ and $R_3$ are 4-methoxybenzyl.

12. A method for regulating the growth of plants which comprises applying to said plants a growth-regulating amount of a compound of the formula of claim 1.

13. The method of claim 12, wherein in said compound Y is $OR_3$.

14. The method of claim 13, wherein
- X represents chlorine or bromine; and each of $R_1$, $R_2$, $R_3$ represents unsubstituted alkyl of from 6 to 18 carbon atoms; $C_1$–$C_{18}$ alkyl substituted by chlorine, bromine, $C_3$–$C_6$ alkenyloxy, phenoxy, $C_3$–$C_{12}$ cycloalkyl, and $C_1$–$C_8$ alkylthio, $C_3$–$C_{18}$ alkenyl; $C_3$–$C_8$ alkynyl; $C_3$–$C_{12}$ cycloalkyl; phenyl; phenyl substituted by alkyl of from 1 to 4 carbon atoms, chlorine, bromine, $C_1$–$C_6$ fluoro-, chloro-, bromoalkyl, alkoxy of from 1 to 4 carbon atoms, and alkylthio of from 1 to 8 carbon atoms, benzyl; and benzyl substituted by alkyl of from 1 to 4 carbon atoms, alkoxy of from 1 to 4 carbon atoms, chlorine and bromine.

15. The method of claim 14, wherein
- $R_1$, $R_2$ and $R_3$ are the same and represent unsubstituted alkyl of from 6 to 18 carbon atoms; $C_1$–$C_6$ fluoro-, chloro-, bromo-alkyl; $C_3$–$C_{18}$ alkenyl; $C_3$–$C_{18}$ fluoro-, chloro-, bromo-alkenyl; $C_3$–$C_8$ alkinyl, or benzyl optionally substituted by alkyl of from 1 to 4 carbon atoms, alkoxy of from 1 to 4 carbon atoms, chlorine and bromine.

16. The method of claim 14, wherein $R_1$, $R_2$ and $R_3$ are the same and represent $C_6$–$C_{18}$ unsubstituted alkyl, $C_1$–$C_6$ fluoro-chloro-bromo-alkyl and $C_1$–$C_{18}$ alkyl substituted by $C_1$–$C_8$ alkylthio.

17. A composition for the regulation of plant growth comprising a) an inert carrier and b) as active ingredient, an effective amount of a compound of the formula of claim 1.

18. The composition of claim 17, wherein in said compound Y is $OR_3$.

19. The composition of claim 18, wherein
- X represents chlorine or bromine; and each of $R_1$, $R_2$, $R_3$ represents unsubstituted alkyl of from 6 to 18 carbon atoms; $C_1$–$C_{18}$ alkyl substituted by chlorine, bromine, $C_3$–$C_6$ alkenyloxy, phenoxy, $C_3$–$C_{12}$ cycloalkyl, and $C_1$–$C_8$ alkylthio, $C_3$–$C_{18}$ alkenyl; $C_3$–$C_8$ alkynyl; $C_3$–$C_{12}$ cycloalkyl; phenyl; phenyl substituted by alky of from 1 to 4 carbon atoms, chlorine, bromine, $C_1$–$C_6$ fluoro-, chloro-, bromoalkyl, alkoxy of from 1 to 4 carbon atoms, and alkylthio of from 1 to 8 carbon atoms, benzyl; and benzyl substituted by alkyl of from 1 to 4 carbon atoms, alkoxy of from 1 to 4 carbon atoms, chlorine and bromine.

20. The composition of claim 18, wherein
- $R_1$, $R_2$ and $R_3$ are the same and represent unsubstituted alkyl of from 6 to 18 carbon atoms; $C_1$–$C_6$ fluoro-, chloro-, bromo-alkyl; $C_3$–$C_{18}$ alkenyl; $C_3$–$C_{18}$ fluoro-, chloro-, bromo-alkenyl; $C_3$–$C_8$ alkinyl; or benzyl optionally substituted by alkyl of from 1 to 4 carbon atoms, alkoxy of from 1 to 4 carbon atoms, chlorine and bromine.

21. The composition of claim 18, wherein
- $R_1$, $R_2$ and $R_3$ are the same and represent $C_6$–$C_{18}$ unsubstituted alkyl, $C_1$–$C_6$ fluoro-, chloro-, bromo-alkyl and $C_1$–$C_{18}$ alkyl substituted by or $C_1$–$C_8$ alkylthio.

* * * * *